US011639490B2

(12) United States Patent
Andriolo et al.

(10) Patent No.: US 11,639,490 B2
(45) Date of Patent: May 2, 2023

(54) DEVICE AND METHOD FOR PRODUCING AND PURIFYING EXOSOMES

(71) Applicant: Foundation for Cardiological Research and Education (FCRE), Lugano (CH)

(72) Inventors: Gabriella Andriolo, Massagno (CH); Elena Provasi, Cislago (IT); Andrea Brambilla, Pessano County Bornago (IT); Viviana Giovanna Lo Cicero, Breganzona (CH); Sabrina Soncin, Daverio (IT); Lucio Barile, Canobbio (CH); Lucia Turchetto, Como (IT); Marina Radrizzani, Cantu' (IT); Giuseppe Vassalli, Sorengo (CH)

(73) Assignee: Foundation for Cardiological Research and Education (FCRE), Lugano (CH)

( * ) Notice: Subject to any disclaimer, the term of this patent is extended or adjusted under 35 U.S.C. 154(b) by 770 days.

(21) Appl. No.: 16/499,532

(22) PCT Filed: Dec. 28, 2017

(86) PCT No.: PCT/EP2017/084747
§ 371 (c)(1),
(2) Date: Sep. 30, 2019

(87) PCT Pub. No.: WO2018/177583
PCT Pub. Date: Oct. 4, 2018

(65) Prior Publication Data
US 2020/0283715 A1    Sep. 10, 2020

(30) Foreign Application Priority Data

Mar. 30, 2017  (CH) .................................... 00424/17
Mar. 30, 2017  (IT) ........................ 102017000035315

(51) Int. Cl.
*C12M 1/00* (2006.01)
*C12M 3/00* (2006.01)
*C12N 5/077* (2010.01)

(52) U.S. Cl.
CPC ............ *C12M 29/16* (2013.01); *C12M 23/42* (2013.01); *C12M 29/04* (2013.01); *C12N 5/0657* (2013.01)

(58) Field of Classification Search
CPC ...... C12M 29/16; C12M 29/04; C12M 23/42; C12N 5/065
(Continued)

(56) References Cited

U.S. PATENT DOCUMENTS 6,812,023 B1    11/2004  Lamparski et al.
2016/0160181 A1*   6/2016  Kreke .................. C12N 5/0657
                                                514/44 A

FOREIGN PATENT DOCUMENTS

WO    2014/028493 A2    2/2014
WO    2016/090183 A1    6/2016

OTHER PUBLICATIONS

Barile, L., et al., "Ultrastructural Evidence of Exosome Secretion by Progenitor Cells in Adult Mouse Myocardium and Adult Human Cardiospheres" Journal of Biomedicine and Biotechnology, pp. 1-10 (2012) cited in Specification.
(Continued)

*Primary Examiner* — Michael L Hobbs
*Assistant Examiner* — Lenora A Abel
(74) *Attorney, Agent, or Firm* — Troutman Pepper Hamilton Sanders LLP

(57) ABSTRACT

The invention discloses a device and method for producing and purifying exosomes from progenitor cells using a closed and sterile circuit having a pumping means and a plurality of serially connected processing stations.

8 Claims, 15 Drawing Sheets

(58) Field of Classification Search
USPC .......................................................... 435/366
See application file for complete search history.

(56) References Cited

OTHER PUBLICATIONS

Barile, L. et al., "Exosomes: Therapy delivery tools and biomarkers of diseases" Pharmacology & Therapeutics, 174:63-78 (2017) cited in Specification.
Cervio, E., et al., "Exosomes for Intramyocardial Intercellular Communication" Stem Cells International, 482171:1-10 (2015) cited in Specification.
Lener, T., et al., "Applying extracellular vesicles based therapeutics in clinical trials—an ISEV position paper" JOurnal of Extracellular Vesicles, 4(30087):31 pages (2015) cited in Specification.
Lotvall, J., et al., "The launch of Journal of Extracellular Vesicles (JEV), the official journal of the International Society for Extracellular Vesicles—about microvesicles, exosomes, ectosomes and other extracellular vesicles" Journal of Extracellular Vesicles, 1(18514):2 pages(2014) cited in Specification.
Mitja L. Heinemann et al: "Benchtop isolation and characterization of functional exosomes by sequential filtration" Journal of Chromatography A, vol. 1371, Dec. 1, 2014 (Dec. 1, 2014), pp. 125-135, XP055372708 cited in ISR and Written Opinion issued in PCT/EP2017/084747 dated Mar. 16, 2018.
Francesco Angelini et al: 11 Exosomes isolation protocols facts and artifacts for cardiac regeneration, Frontiers in Bioscience (Scholar Edition), vol. 8, No. 2, Jun. 1, 2016 (Jun. 1, 2016), pp. 303-311, XP055417663 cited in ISR and Written Opinion issued in PCT/EP2017/084747 dated Mar. 16, 2018.
Pin Li et al: "Progress in Exosome Isolation Techniques", Theranostics, vol. 7, No. 3, Jan. 1, 2017 (Jan. 1, 2017), pp. 789-804, XP055417509 cited in ISR and Written Opinion issued in PCT/EP2017/084747 dated Mar. 16, 2018.

Rafal Szatanek et al: "Isolation of extracellular vesicles: Determining the correct approach (Review)", International Journal of Molecular Medicine, vol. 36, No. 1, Jul. 1, 2015 (Jul. 1, 2015), pp. 11-17, XP055409099 cited in ISR and Written Opinion issued in PCT/EP2017/084747 dated Mar. 16, 2018.
Emily Zeringer et al: "Strategies for Isolation of Exosomes", Cold Spring Harbor Protocol, vol. 2015, No. 4, Apr. 1, 2015 (Apr. 1, 2015), XP055417515 cited in ISR and Written Opinion issued in PCT/EP2017/084747 dated Mar. 16, 2018.
L. Barile et al: "Extracellular vesicles from human cardiac progenitor cells inhibit cardiomyocyte apoptosis and improve cardiac function after myocardial infarction", Cardiovascular Research, vol. 103, No. 4, Jul. 11, 2014 (Jul. 11, 2014), pp. 530-541, XP055417520 cited in ISR and Written Opinion issued in PCT/EP2017/084747 dated Mar. 16, 2018.
Ahmed Gamal-Eldin Ibrahim et al: "Exosomes as Critical Agents of Cardiac Regeneration Triggered by Cell Therapy", Stem Cell Reports, vol. 2, No. 5, May 1, 2014 (May 1, 2014), pp. 606-619, XP055335389 cited in ISR and Written Opinion issued in PCT/EP2017/084747 dated Mar. 16, 2018.
Chen Lijuan et al: "Cardiac progenitor-derived exosomes protect ischemic myocardium from acute ischemia/reperfusion injury", Biochemical and Biophysical Research Communications, Elsevier, Amsterdam, NL, vol. 431, No. 3, Jan. 11, 2013 (Jan. 11, 2013), pp. 566-571, XP028980130 cited in ISR and Written Opinion issued in PCT/EP2017/084747 dated Mar. 16, 2018.
Lucio Barile et al: "Roles of exosomes in cardioprotection", European Heart Journal, Jul. 21, 2016 (Jul. 21, 2016), p. ehw304, XP055417503, 38:1372-1387 cited in ISR and Written Opinion issued in PCT/EP2017/084747 dated Mar. 16, 2018.
International Search Report and Written Opinion issued in corresponding International Patent Application No. PCT/EP2017/084747 dated Mar. 16, 2018.

* cited by examiner

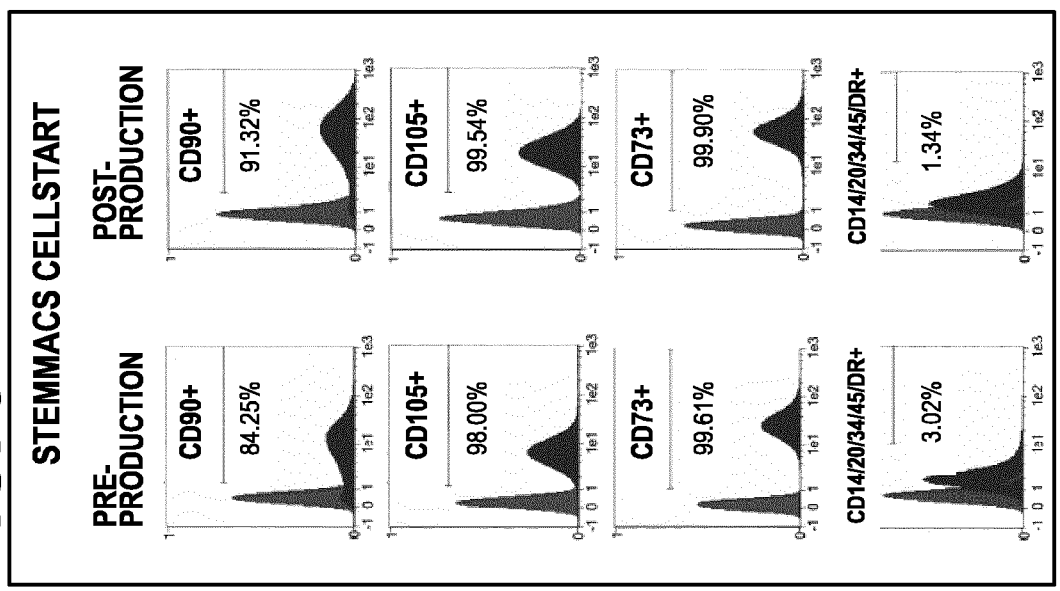
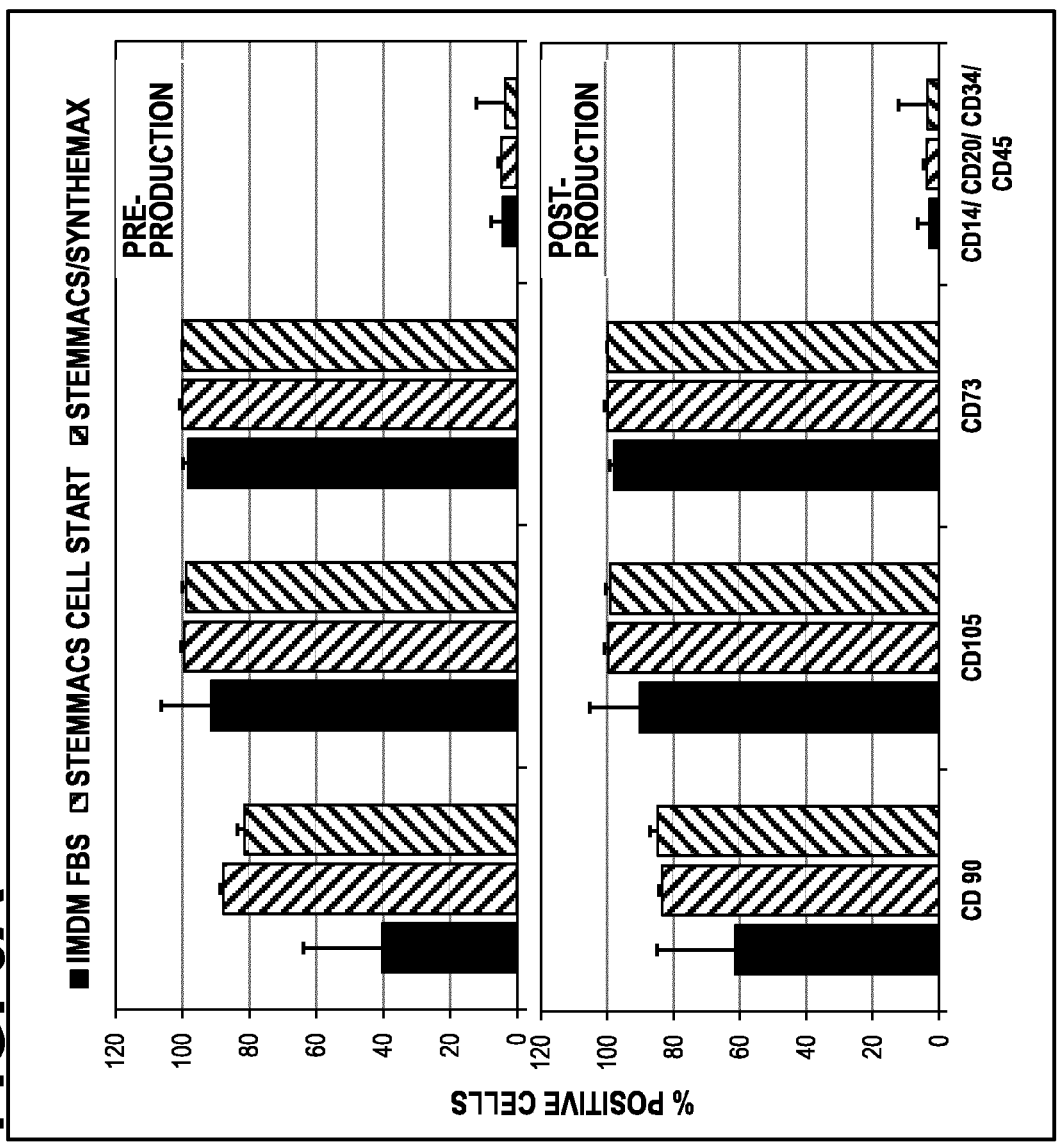

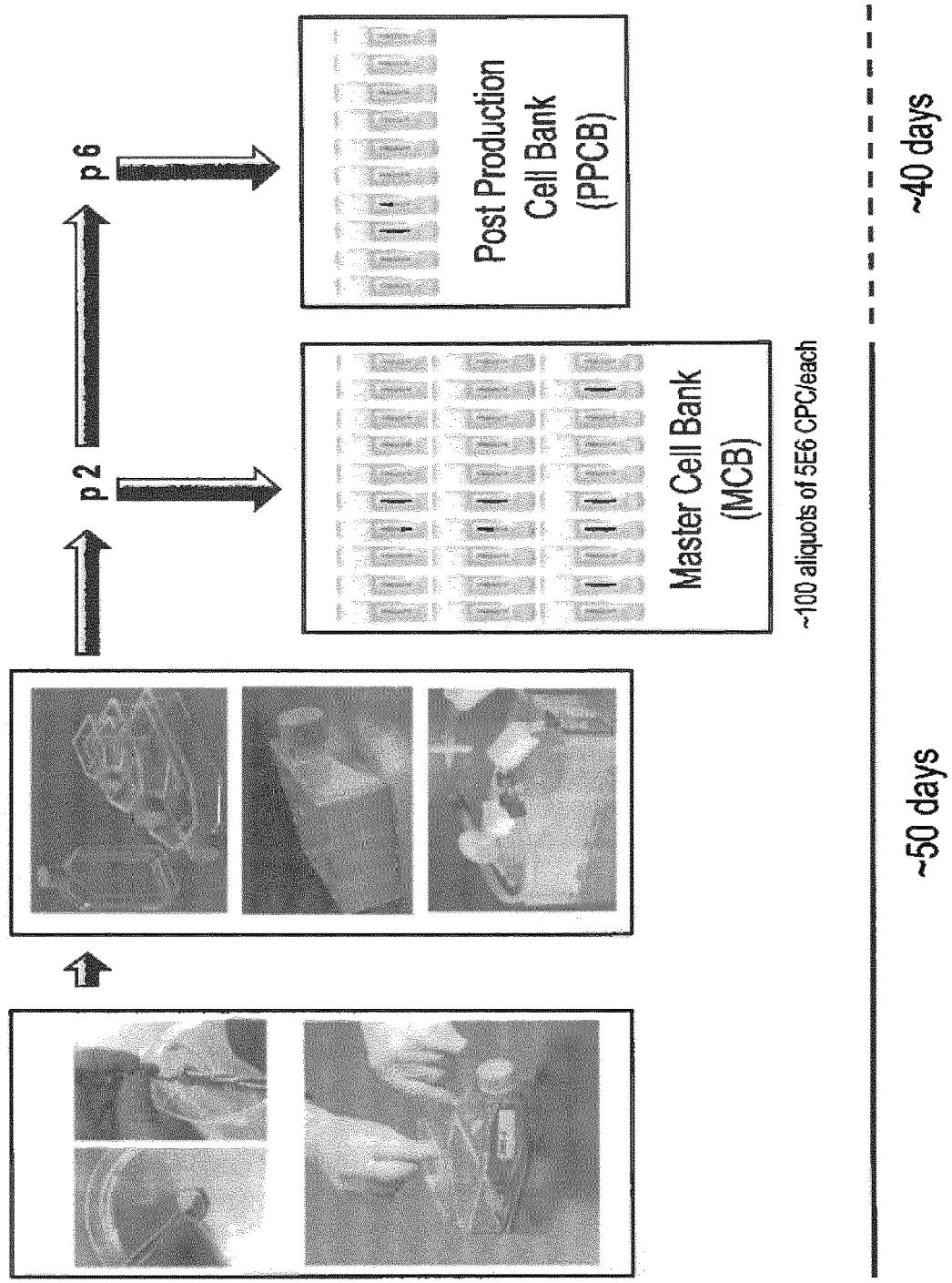

DEVICE AND METHOD FOR PRODUCING AND PURIFYING EXOSOMES

CROSS REFERENCE TO RELATED APPLICATIONS

This is a U.S. National Phase application under 35 U.S.C. § 371 of International Patent Application No. PCT/EP2017/084747, filed Dec. 28, 2017, which claims priority of Swiss Patent Application No. 00424/17, filed Mar. 30, 2017 and Italian Patent Application No. 102017000035315, filed Mar. 30, 2017. The entire contents of which are hereby incorporated by reference.

FIELD OF THE INVENTION

The present invention relates to a device and a method for producing and purifying exosomes from progenitor cells.

BACKGROUND

Exosomes are extracellular vesicles with a diameter of 30-150 nm, involved in intercellular communication processes. They are of endosomal origin and are secreted by many types of cell; they express characteristic markers, such as CD9, CD63, CD81, Alix and TSG-101, as well as typical markers of the cells from which they originate, which also determine the microRNA content (Cervio E et al 2015, *Stem Cells International*; Barile L et al 2016, *Eur Heart J*).

Exosomes are currently the subject matter of various studies that aim to clarify their role, action mechanisms and potential diagnostic and therapeutic applications (Lener et al 2015, *J Extracell Vesicle*, Barile et al. 2017 *Pharmacol Ther.*).

In the laboratories of the Cardiocentro Ticino/Swiss Institute for Regenerative Medicine (CCT/SIRM), in collaboration with the "Victor Babes" National Institute of Pathology in Bucharest, Romania, the first scientific evidence has been produced, through electronic microscopy, that human cardiac progenitor cells (CPC) release extracellular vesicles with typical characteristics of exosomes (Barile et al. 2012 *J Biomed Biotechnol*). At the Cardiocentro Ticino it has also been demonstrated that such vesicles inhibit cardiomyocyte apoptosis and promote angiogenesis, hence playing a fundamental role in the paracrine effect of CPCs. Also in vivo, in a pre-clinical model of acute myocardial infarction in rats, exosomes deriving from CPCs reduce tissue damage, inhibit cardiomyocyte apoptosis and promote angiogenesis, improving post-infarction cardiac function.

Key mediators of these effects could be some specific microRNAs such as miR-132 and miR-210 (Bartle L et al 2014, *Cardiovasc Res*).

SUMMARY

CPC-derived exosomes therefore represent a promising candidate for future clinical applications, based on an alternative and innovative approach with respect to cell therapies currently studied in the cardiovascular field. With respect to a cell product, isolated exosomes could have advantages in terms of safety and manageability. They could be used both in an autologous and an allogenic context; in particular, allogenic use would allow a frozen product to be made available, ready for use, that could be used in situations of acute damage.

From this perspective, in the laboratories of the Lugano Cell Factory-Cardiocentro Ticino (LCF-CCT) the focus has been on the development of closed circuit production methods and quality control for the large-scale preparation of CPC-derived exosomes as a medicinal product, in accordance with Good Manufacturing Practices, (GMPs). Current techniques for producing exosomes fall into the category of all the processes known as "research grade" which are normally used for preparing exosomes for the first pre-clinical studies. (Bartle L et al 2014, *Cardiovasc Res*).

An example of this process is depicted in FIG. 1, and consists of two distinct steps, respectively (A) isolation and expansion of CPC starting from cardiac tissue and (B) isolation of exosomes starting from the conditioned medium of the CPCs. Step A. The cells are obtained starting from cardiac tissue (atrial appendage) which represents "waste" during heart surgery operations; the patient/donor signs an informed consent form for the donation of such tissue for research purposes.

The tissue is processed by cutting it into small fragments, which are placed to adhere in a gelatin-coated plate (Sigma), in the presence of IMDM culture medium (Lonza) with 20% foetal bovine serum (FBS) added (Gibco/ThermoFisher) and incubated at 37° C. with 5% $CO_2$. After some days, the leakage of cells (CPCs) is observed at the sides of the fragments, expanding until they cover the surface of the plate itself. The CPCs are then harvested through treatment with trypsin (Sigma), then re-inseminated in appropriate flasks and expanded in IMDM 20% FBS at 37° C. with 5% $CO_2$ (CPC first harvest). The fragments remaining in the original plate are left in adhesion, in the presence of new IMDM 20% FBS medium; after some days the leakage of cells is observed again, expanding until they cover the surface of the plate itself. The CPCs are then harvested through treatment with trypsin, then re-inseminated in appropriate flasks and expanded in IMDM 20% FBS at 37° C. with 5% $CO_2$ (CPC second harvest). The process is repeated for a third time (CPC third harvest).

Step B. For producing exosomes, a flask with CPCs (deriving from the first, second or third harvest) at confluency is maintained for 7 days in DMEM medium with glucose 4.5 g/L (Gibco/ThermoFisher) in the absence of serum; then the conditioned medium (CM), which contains the exosomes, is harvested; the CM is centrifuged at 3000×g and filtered (0.22 µm) then concentrated through centrifugation at 3000×g in Amicon Ultra-15, cut-off 100 KD (Merck Millipore). The concentrate is centrifuged again at 10000×g, the supernatant harvested and ultra-centrifuged at 100000×g, in order to obtain a precipitate containing exosomes, which are then re-suspended in phosphate buffered saline (PBS).

The "research grade" process has some critical elements, i.e. aspects that are not compatible with translation into the clinical setting.

In particular, the use of reagents of animal origin for the isolation and culture of the CPCs can put the safety of the product at risk, while the performance of multiple harvests can put the homogeneity at risk.

The use of centrifugation and ultra-centrifugation passages during the process for preparing the exosomes limits the maximum scale of the process itself to 1-2 L of CM.

The technical task underpinning the invention is therefore to develop a device and a method for the production, purification and quality control of exosomes on a large scale as a medicinal product to be used in the clinical phase.

Within the context of this technical task, an object of the present invention is to provide a device and method for producing exosomes on a large scale in accordance with Good Manufacturing Practices.

Another object of the invention is to provide a closed-circuit device that guarantees the sterility of the product, and a method for producing and purifying exosomes for the preparation of exosomes ready to be used as a medicinal product, in disposable packages.

These and other objects of the present invention are achieved by a device for producing and purifying exosomes from progenitor cells wherein it comprises a closed and sterile circuit having a pumping means and a plurality of serially connected processing stations wherein a first processing station comprises a first culture medium containing said progenitor cells, which are cultured for the production of said exosomes;

a second processing station comprises a second medium conditioned by the exosomes produced in the first processing station;

a third processing station comprises a filtering means for clarifying said conditioned medium;

a fourth processing station comprises one or more hollow fiber cartridges for concentrating the clarified conditioned medium by tangential filtration and a means for recirculating the concentrated medium for a subsequent concentration thereof;

a fifth processing station comprises a formulation buffer for diluting the concentrated medium;

a sixth processing station comprises waste material output from said fourth processing station;

a seventh processing station comprises a means for collecting the diafiltered-concentrated medium containing the purified exosomes;

an eighth processing station comprises a storage means for storing said purified exosomes.

The invention further discloses a method for producing and purifying exosomes from progenitor cells wherein it is performed in a closed and sterile system and envisages the following steps:

a step of producing a conditioned medium containing said exosomes by culturing said progenitor cells in a first culture medium;

a step of clarifying said conditioned medium by passage, in series, through a plurality of filters;

a step of collecting the clarified conditioned medium;

a step of concentrating the conditioned medium by tangential filtration through hollow fiber cartridges with a cut-off comprised between 100 and 500 KD;

a step of recirculating said filtered conditioned medium for a greater concentration thereof;

a step of discarding particulate material whose dimensions are smaller than the cut-off of the hollow fiber cartridge;

a step of diafiltering said concentrated medium through a hollow fiber cartridge with a cut-off comprised between TOO and 500 KD via a sterile connection with a formulation buffer;

a step of recovering the diafiltered-concentrated medium containing purified exosomes;

a step of storing said purified exosomes in suitable containers.

The different steps are designed to be "modular" in order to be possibly automated in the future, individually or in combination in a single device.

DESCRIPTION OF THE DRAWINGS

Other main aspects of the invention are reported in the following dependent claims. These and other aspects of the invention will be more fully clarified upon reading of the following description of a preferred embodiment thereof, in which:

FIG. 6a and FIG. 6b show the results obtained from immunophenotyping, before and after the production of exosomes, through coloring with fluorescent antibodies (MSC phenotyping kit, Miltenyi Biotec) and cytofluorimetric analysis (MACSQuant Analyzer 10, Miltenyi Biotec), respectively in terms of percentage of positive cells and histograms related to the fluorescence intensity for the different markers.

FIG. 15 shows the preparation of cell banks of cardiac progenitor cells.

DETAILED DESCRIPTION

Figure 1:
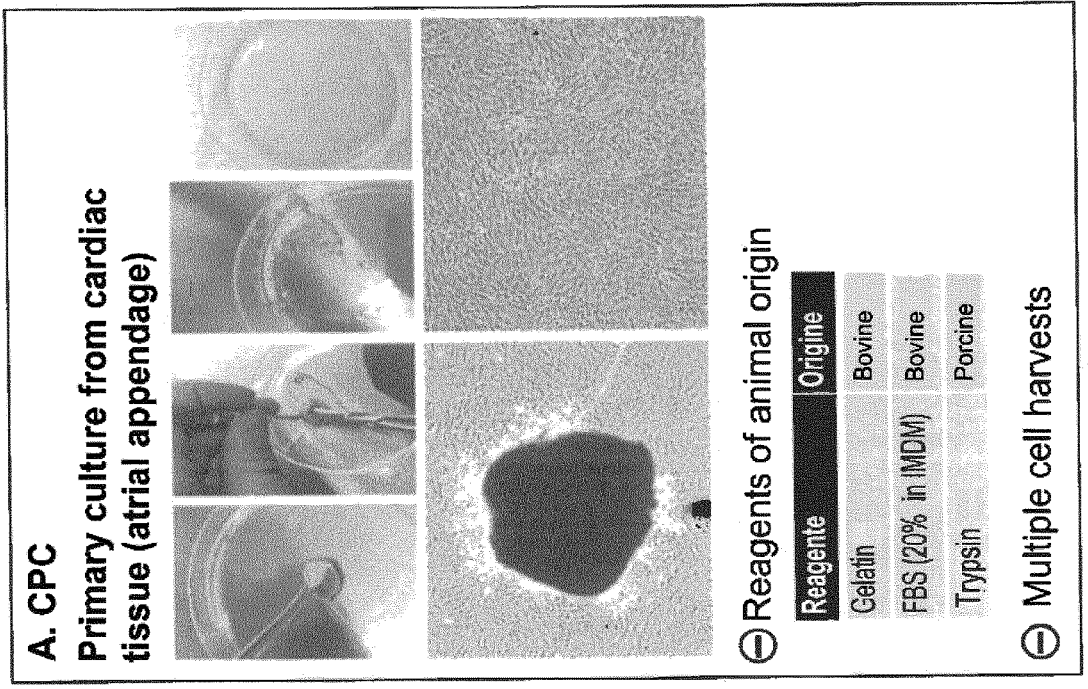
FIG. 1 shows the research grade process according to the prior art for producing exosomes from cardiac progenitor cells.

The experimental approach used for the development of the device and method for producing and purifying exosomes according to the present invention is depicted in Table 1 below.

TABLE 1

| From: | To: |
|---|---|
| CPC | |
| Gelatin | Alternative adhesion substrates: CELLStart ™CTS ™ (Gibco/ThermoFisher) Synthemax II ® (Corning) CellBIND ® surface (Corning) |
| IMDM-FBS | Culture medium free from serum and components of animal origin: StemMACS-MSC Expansion Media Kit XF (Miltenyi Biotec) |
| Trypsin | Alternative dissociation systems: TripLE ™ Select (Gibco/ThermoFisher) |
| Multiple cell harvests | Single cell harvest |
| | EXOSOMES |
| Ultracentrifugation | Alternative enrichment methods Concentration through direct or tangential filtration |

Gelatin (of bovine origin) was replaced with alternative adhesion substrates as indicated in the Table, which are free from components of animal origin; the IMDM 20% FBS medium (of bovine origin) was replaced with a serum-free culture medium free from animal components, selected from 7 different commercial products; trypsin (of porcine origin) was replaced with the alternative reagent TripLE Select; a single harvest of CPC is performed instead of the 3 envisaged in the "research grade" process; ultracentrifugation was replaced with alternative enrichment/purification methodologies, such as concentration through direct or tangential flow filtration.

The isolation and culture of the CPCs were performed in parallel, starting from the same sample of cardiac tissue, in "research" conditions (culture medium with FBS, gelatin adhesion substrate) and in two different "pre-GMP" conditions (serum-free medium, adhesion substrate respectively CELLStart™ CTS™ and Synthemax® II); the experiment was repeated 5 times, using samples of cardiac tissue taken from 5 different patients/donors, in the context of a study authorized by the Ethics Committee.

The device 1 for producing and purifying exosomes from progenitor cells comprises a closed and sterile circuit having a pumping means 9, 10 and a plurality of serially connected processing stations 2, 3, 4, 5, 7, 8, 11 and 12.

In particular, the first processing station 2 comprises a first culture medium in which the progenitor cells (hereinafter CPs) are cultured for the production of the exosomes.

The second processing station 3 instead comprises a second conditioned medium, containing the exosomes produced in the first processing station.

The third processing station 4 comprises a plurality of filters arranged in series for clarifying the conditioned medium.

The fourth processing station 5 comprises a hollow fiber cartridge 6 for concentrating the clarified conditioned medium by tangential filtration and a means for recirculating the concentrated medium filtered on the hollow fiber cartridge for a subsequent concentration thereof.

The fifth processing station 12 comprises a formulation buffer for diluting the concentrated conditioned medium.

The sixth processing station 7 comprises waste material output from the fourth processing station.

The seventh processing station 8 comprises a means for collecting the diafiltered-concentrated medium containing said purified exosomes.

Finally, the eighth processing station 11 comprises a storage means for storing said purified exosomes.

In particular, the pumping means 9, 10 comprises a peristaltic or diaphragm pump. In the present invention the progenitor cells are cardiac progenitor cells. The device and the method for producing and purifying exosomes can also be used for many other types of cells.

The present invention wherein the passage of fluid containing exosomes from the first processing station 2 to storage in the relevant containers is performed by means of bags.

In particular, the second processing station 3 comprises a bag for collecting the conditioned medium containing the exosomes produced by the CPs. The fourth processing station 5 comprises a bag for collecting the clarified conditioned medium called the "process bag". The fifth processing station 12 comprises a bag containing a formulation buffer for diluting the concentrated medium coming from the process bag.

The sixth processing station 7 comprises a waste bag for collecting the waste material coming from the fourth processing station 5. Finally, the seventh processing station 8 comprises a bag, called "finished product bag" for collecting the purified exosomes.

Advantageously, the recirculating means 10 comprises a peristaltic or diaphragm pump.

The hollow fiber has a cut-off comprised between 100 and 500 KD, preferably 300 KD.

The storage containers comprise sterile vials made of polymer resistant to cryogenic temperatures.

More details of the present invention will be highlighted further in the following description of a preferred embodiment of the invention.

Source of Cells

Biopsies from the right atrial auricle of the heart are obtained from patients, not carrying concomitant pathologies to the coronary arteries, subjected to heart valve repair surgery. The tissue was taken in accordance with the Helsinki Declaration and in accordance with a specific authorization by the local Ethics Committee, based on informed consent.

The biopsy, received in a sterile container containing cardioplegic solution (Plasmalyte A 1000 mL+20% Mannitol 16 mL+50% Magnesium Sulphate 4 mL+8.4% Sodium Bicarbonate 13 mL+1% Lidocaine13 mL+2M Potassium Chloride 13 mL), is processed in sterile conditions (Class A laminar flow hood): 2 washes are performed with Dulbecco phosphate buffered saline without Calcium and Magnesium (DPBS, Gibco Invitrogen cell culture, Thermo Fisher Scientific, USA) and the muscle tissue is isolated from the connective tissue after the transfer of the biopsy onto a sterile medium (Petri dish, Corning, USA); the muscle tissue is then mechanically ground to obtain fragments with a maximum dimension of 0.5-1 mm.

The fragments of tissue transferred into a clean Petri dish, after being washed twice with DPBS, are subjected to treatment with about 1-2 mL of enzyme solution (TrypLE™ Select Enzyme IX, no phenol red, Thermo Fisher Scientific, USA) and incubated for 10 minutes at ambient temperature. Then the enzyme solution is removed and the fragments are re-suspended in about 2 mL of culture medium MSC-BREW GMP Medium (Miltenyi Biotec, Germany).

The biopsy fragments obtained are positioned according to a lattice (16 fragments/flask) in the presence of 4-5 mL of culture medium in Tl 15 flasks with a upward opening door (TPP®, Sigma-Aldrich Chemie GmbH, Germany), previously treated with CELLstart™ CTS™ (Gibco Invitrogen cell culture, Thermo Fisher Scientific, USA) for 2 hours at 37° C. 5% $CO_2$ according to the manufacturer's instructions. The flasks are incubated at 37° C. 5% $CO_2$ and daily, with caution so as not to let the fragments adhering to the surface of the flask detach, 1-2 mL of culture medium is added until 10 mL of medium per flask is reached.

Figure 14B:
FIGS. 14A and 14B respectively show the leakage of cardiac progenitor cells from a biopsy fragment and the expansion of the cardiac progenitor cells in culture medium in pre-GMP conditions.
Figure 14A:
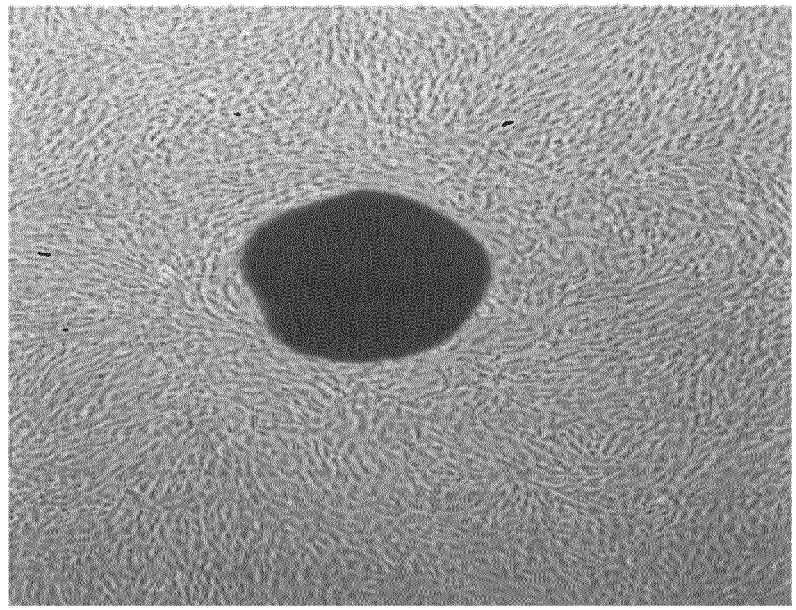

After about 14-21 days from the adhering biopsy fragments leakage of the CPCs is observed, as shown in FIG. 14 A.

Cell Culture and Establishment of the Master Cell Bank

The cells are detached from the flasks containing the biopsy fragments with the TrypLE™ Select Enzyme 1× solution, plated again at the concentration of $8-10\times10^3$ cells/cm² in a T flask, Hyperflask, Hyperstack or CellStack (Corning, USA), cultivated with culture medium MSC-BREW GMP Medium and expanded until the 2nd culture passage (P2). FIG. 14 B shows the CPCs in culture in GMP conditions.

At the culture passage P2 the cells are frozen to constitute the ""Master Cell Bank" (MCB, FIG. 15) after re-suspension in Cryostor® CS10 (BioLife Solutions, USA), by means of freezing through temperature-programmed reduction (Biofreeze® BV45, Consartic, Germany). A fraction of the cells is re-inseminated and maintained in culture for another 4 passages (until P6), to construct the "Post Production Cell Bank" (PPCB, FIG. 15), i.e. a small bank of CPCs maintained in culture long after passage P4 in which the production of exosomes is performed; the PPCB is controlled (see quality control chapter) in particular for the safety aspects.

Figure 13:
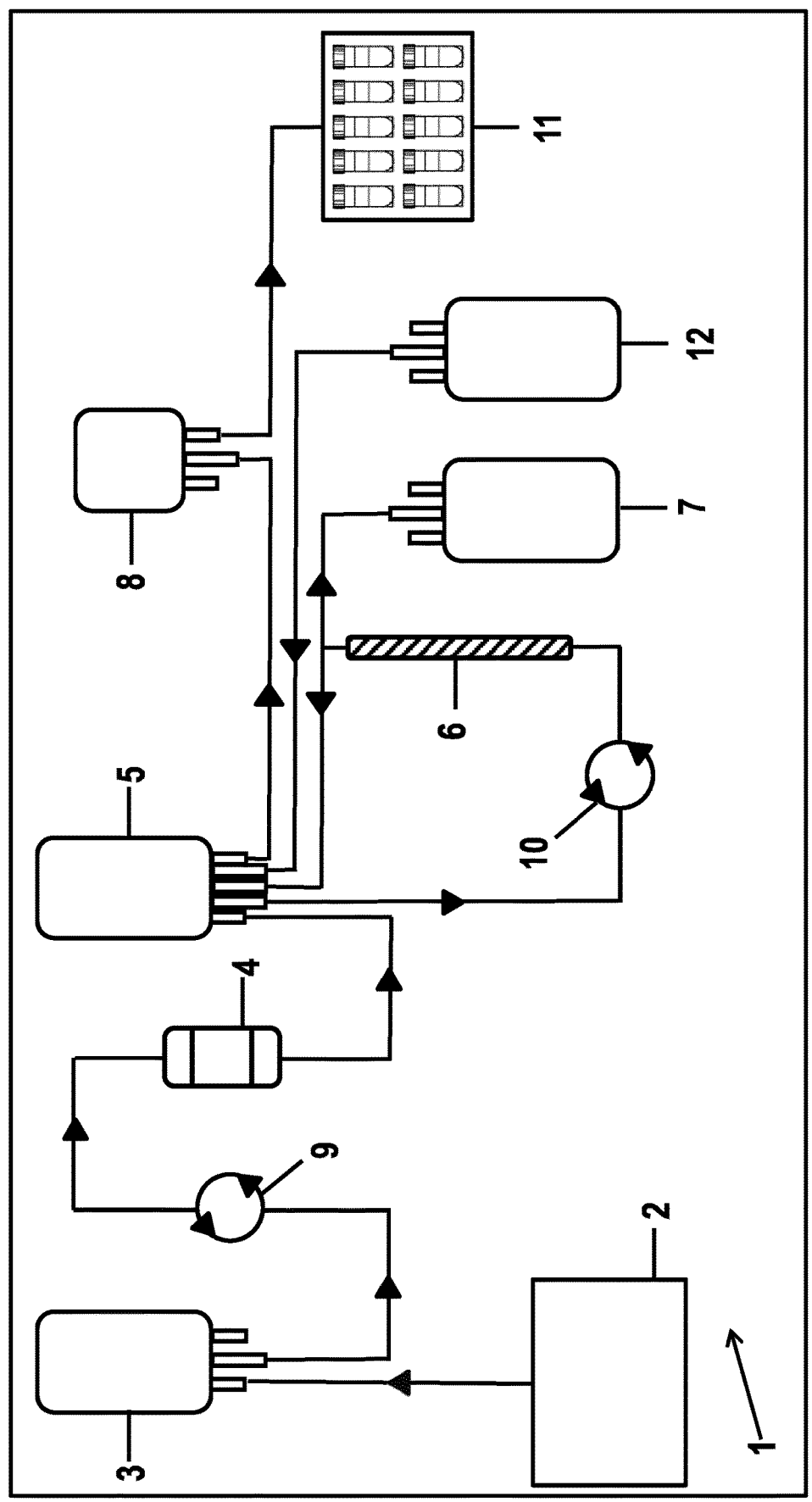
FIG. 13 shows a diagram of the method for producing and purifying exosomes according to the present invention.

Production of Exosomes in the Culture Medium and Clinical-Grade Second System Purification The production process of exosomes starting from the CPC MCB is depicted in FIG. 13 and described in detail below.

An aliquot of CPCs frozen in the MCB is defrosted and the CPCs are cultivated ($8-10\times10^3$ cells/cm² initial insemination) with the culture medium MSC-BREW GMP Medium through the HYPERFlask® culture system and 12 layer HYPERStack® CELLBIND® (Corning, USA), until the 4th passage (P4).

At passage P4 the culture medium is replaced in a closed system through the use of bags, after washing twice with DPBS, with the basal medium MSC-BREW GMP without the addition of supplements or DMEM with a high glucose content (4.5 g/L) no phenol red (Gibco Invitrogen cell culture, Thermo Fisher Scientific, USA).

The cells are incubated for 1 week at 37° C. 5% $CO_2$ without changing the medium. The volumes of conditioned medium containing the exosomes produced with this system may be 0.5-8 L. In the event of using a bioreactor the volumes of conditioned medium produced will be higher.

The conditioned medium is collected in sterile conditions through bag connection. Then, the End of Production Cells (EPCs) are detached as described above and frozen after re-suspension in Cryostor® CS10 (BioLife Solutions, USA), through a temperature-programmed reduction freezer (Biofreeze® BV45, Consartic, Germany); the EPCs are then subjected to quality control tests.

The purification process is performed in a closed system using an ÄKTA™ flux 6 (GE Healthcare) instrument with a kit of bags connected under sterile conditions to the system, made especially for our laboratory and for this type of clinical-grade purification of exosomes starting from the conditioned medium.

The purification of the exosomes from the conditioned medium envisages the following passages performed in sequence in a closed and sterile system, in particular using the ÄKTA™ flux 6 machine (FIG. 13), whose internal circuits have been subjected to appropriate sanitization, and ReadyMate (GE Healthcare) connections:

STEP 1 CLARIFICATION: the bag containing the conditioned medium is connected under sterile conditions to the machine circuit to perform clarification through passage in series onto the 0.6-0.2 μm filters thanks to the use of the machine transfer pump (or with an external peristaltic pump). The clarified medium is collected under sterile conditions in the bag called process bag.

STEP 2 CONCENTRATION: the process bag is sterilely connected in a closed circuit to perform concentration through Tangential Flow Filtration (TFF) on a hollow fiber cartridge with cut-off 300 KD (or 100/500 KD), thanks to the use of the machine loading pump (or with an external peristaltic or diaphragm pump). From the hollow fiber cartridge the material output containing smaller particles than the fiber cut-off goes into the waste bag; the remaining medium returns into the process bag for the performance of new concentration passages. The final volume after concentration is 150-500 mL. The machine parameters (e.g. flow speed, transmembrane pressure) are set so as to minimize shear stress and therefore guarantee the integrity of the exosomes at the end of the process.

STEP 3 DIAFILTRATION: the concentrated medium contained in the process bag is diluted through sterile connection with the formulation buffer (buffer—20 mM TRIS HCl, 1 mM MgCl2, 5% saccharose, 100 mg/mL Human Serum Albumin pH 7.4; or Ringer solution, or PlasmaLite A, or other clinical-grade solutions suitable for in vivo infusion); a series of dilution and concentration passages are performed in order to obtain an initial buffer solution greater than or equal to 95%. The medium contained in the process bag performs the diafiltration passage through passage on the hollow fiber cartridge with cut-off of 300 KD (or 100/500 KD), thanks to the use of the machine loading pump (or with an external peristaltic pump). The final volume obtained is 100-400 mL.

STEP 4 RECOVERY: The product contained in the process bag is recovered through a sterile connection to the final product bag. To increase the safety of the entire process, a sterilizing filtration passage can be performed, by inserting a capsule filter (0.2 μm) into the tube at the inlet to the final product bag and using a pump.

The expected yield of the purification process is equal to about 1 μg of TSG101, corresponding to about 3E12 exosomes, for every liter of conditioned medium processed.

Storage of the Medicinal Product (Purified Exosomes from CPCs)

The suspension containing the purified exosomes is split into aliquots through sterile transfer into primary containers—Crystal® Vials (Aseptic Technologies, Belgium); the containers are then stored at −80° C. or in liquid nitrogen vapors.

GMP Quality Control Strategy

The quality control strategy, depicted in Table 2 was defined considering the peculiar aspects of the medicinal product constituting exosomes from CPCs.

This strategy aims to guarantee maximum product quality in terms of identity/power, purity and safety. It is based on some analytical methods described in the pharmacopoeia and other methods specifically developed or optimized in our laboratories. Appropriate controls are performed on the cells of the MCB and the PPCB, like on every batch of medicinal product (exosomes) and the relative EPCs. The first 3-5 batches of medicinal product prepared starting from MCB are considered validation batches and are subjected to a more extensive control panel, in particular in relation to safety tests, with respect to the subsequent batches.

TABLE 2

| | Parameter/Test | MCB | PPCB | EPC | Exosomes |
|---|---|---|---|---|---|
| Identify/Power | Count and vitality (trypan blue) | X | X | X | |
| | Immunophenotype (FACS) | X | X | X | X |
| | Expression of transcription factors (RT-PCR) | X | X | X | |
| | Concentration and size of exosomes (NTA) | | | | X |
| | TSG101 (ELISA) | | | | X |
| | Inhibition of cell apoptosis | | | | X |
| Purity | Total protein (BCA) | | | | X |
| | Residual DNA | | | | X |
| Safety | Sterility (microbiological examination EP 2.6.27) | X | X | X | X |
| | Endotoxin (LAL test EP 2.6.14) | X | X | X | X |
| | Mycoplasma (PCR) | | | X | X |
| | Mycoplasma (culture test EP 2.6.7) | X | X | [X] | X |
| | Adventitious viruses | X | X | [X] | [X] |
| | Karyotype | X | X | [X] | [X] |
| | Cellular senescence | X | X | [X] | |
| | Tumorigenicity | X | X | [X] | |

[X] only in validation stage

Description of Analytical Methods for GMP Quality Control

The main methods specifically developed or optimized in our laboratories for quality control in GMP of CPCs (MCB, PPCB, EPCs) and of exosomes (medicinal product) are described below.

Immunophenotypical Analysis of CPCs

The surface markers CD73, CD90, CD105, typical of mesenchymal stem cells (MSCs) are evaluated; CD14, CD20, CD34 and CD45 are evaluated as control markers, not expressed on MSCs (Dominici M et al. 2006. Cytotherapy 8:215-217).

The cells are marked using the Miltenyi Biotec kit for MSC and analysed through MACSQuant Analyzer (Miltenyi Biotec).

Examples of results obtained with this test are reported in FIG. 6B.

Analysis of the Expression of Transcription Factors in CPCs: RT-PCR

The genes GATA4 (Gene ID: 2626), TBX5 (Gene ID: 6910), TBX18 (Gene ID: 9096) e MESP1 (Gene ID: 55897) were selected based on literature as mesodermal transcription factors (TBX5, TBX18) and cardiac-specific transcription factors (GATA-4 and MESP1). To control reverse transcription and amplification, direct primers on the GAPDH gene were used (Gene ID: 2597).

The RNA was extracted from the CPCs with the TRIzol® Reagent kit (Thermo Fisher Scientific) and quantified through absorbency at 260 nm. 500 ng of RNA per sample were reverse transcribed with the GoScript™ Reverse Transcription System kit (Promega); for each sample a so-called "RT minus control" was prepared, i.e. a test in which the reverse transcriptase is not added. For each gene, a quantity of cDNA equivalent to 25 ng of starting RNA is then amplified with the GoTaq® DNA Polymerase (Promega) kit on a C1000 thermal cycler (BioRad Laboratories). The PCR products are separated on a 2% agarose gel.

The presence of the specific band in a lane of gel indicates that the RNA of the corresponding gene was expressed in the analyzed sample; instead, in the corresponding RT minus control there should be no band present.

Figure 7:
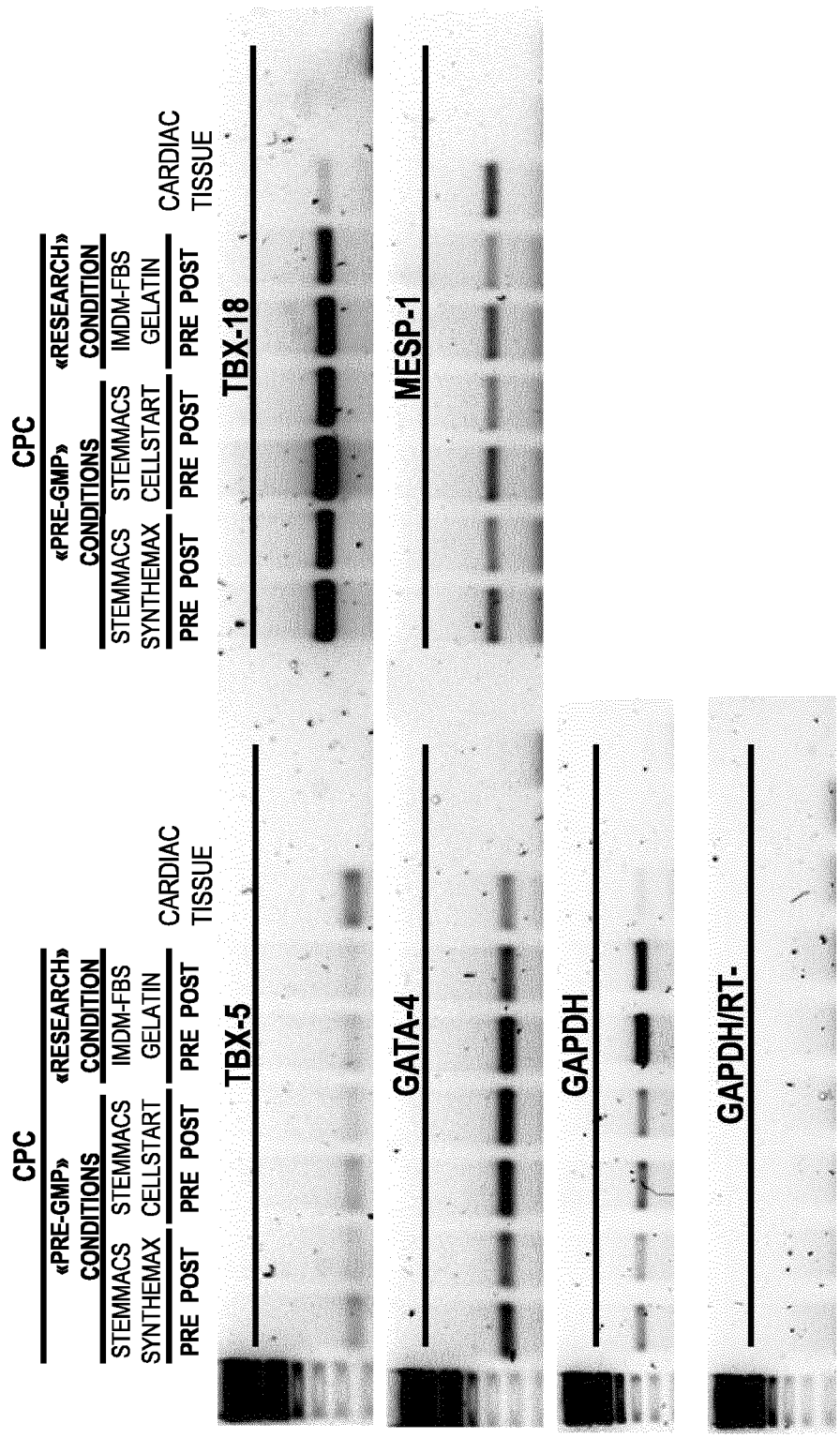
FIG. 7 shows the expression of mesodermal and cardiac-specific transcription factors by cardiac progenitor cells both in "research grade" conditions and according to the present invention (PRE-GMP conditions).

An example of results obtained with this test is reported in FIG. 7.

Western Blot

To check the purity of samples containing exosomes it is also necessary to investigate both the presence of specific markers of the exosome fraction, and the absence, or at least the sub-representation, of cell markers. A list of such markers has been defined by the International Society for Extracellular Vesicles (Lötvall J et al, 2014, *J Extracell Vesicles*).

The preparations of exosomes, and the appropriate positive and negative checks, are subjected to Western Blot analysis for the identification of the following markers:

1. TSG101 (Gene ID: 7251), a protein of the complex ESCRT-I enriched in exosomes
2. HSP90B1 (alias: GPR94, Gene ID: 7184), a molecular chaperone typical of the endoplasmic reticulum, and therefore of the presence of cell culture contaminants in the preparation.

For the electrophoretic separation of the proteins and the Western Blot hybridization, the BioRad-Laboratories (USA) system based on ready-to-use gels (Mini-PROTEAN TGX Stain-Free™ gels) and a Trans-Blot® Turbo™ Transfer System are used. Reference is made to the specific protocols of such kits for performing the experiment.

The presence of the proteins in question is investigated using specific primary and unmarked antibodies, on which a secondary antibody marked with a fluorophore is made to react. The detection system is therefore of the fluorescent type; with equal sensitivity it is also possible to use a method based on the generation of a luminescent signal.

Determination of the Concentration and Size of Exosomes

The test is performed using Nanoparticle Tracking Analysis (NTA).

Figure 8:
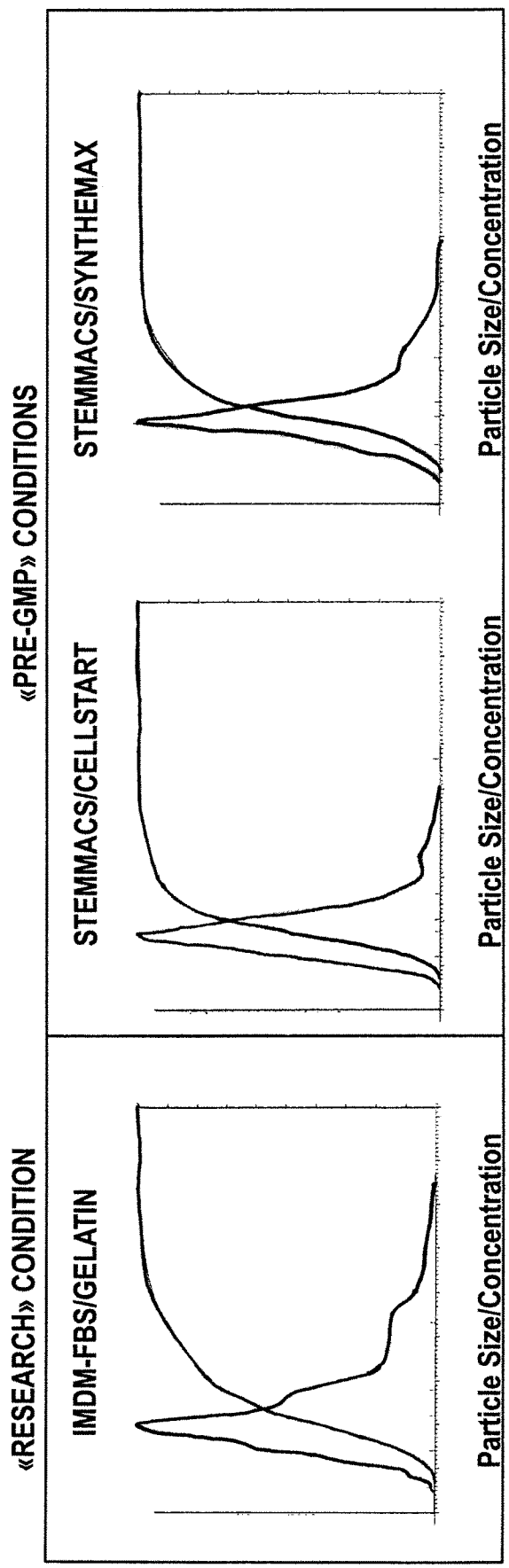
FIG. 8 shows the NTA (Nanoparticle Tracking Analysis) performed on exosomes obtained from cardiac progenitor cells both in "research grade" and PRE-GMP conditions.

By analyzing the light scattering and Brownian motion properties, the NanoSight LM10 instrument (Malvern Instruments) is able to determine their size distribution and concentration. The samples of interest (conditioned medium and purification products) were then analyzed with this instrument, obtaining their titre (in particles/ml) and size distribution (in nm of diameter). Examples of NanoSight tracking are shown in FIG. 8.

ELISA Test for the Quantification of TSG101

The quantification of the exosomes contained in the initial conditioned medium and in the purification products in closed circuit is performed by evaluating the concentration of the protein TSG101, contained inside the exosomal vesicles, through the ELISA TSG101 kit (Sandwich ELISA, LSBio LifeSpan Biosciences Inc, USA).

The kit, a so-called "sandwich ELISA", requires the parallel quantification of unknown samples and of a standard purified protein curve (provided in the kit). It provides a colorimetric reading at 450 nm proportional to the initial concentration of the samples. The absorbency data, after logarithmic transformation, are used to trace the standard curve and to infer the concentration of the protein TSG101 in unknown samples, expressing it in ng/ml.

Figure 11:
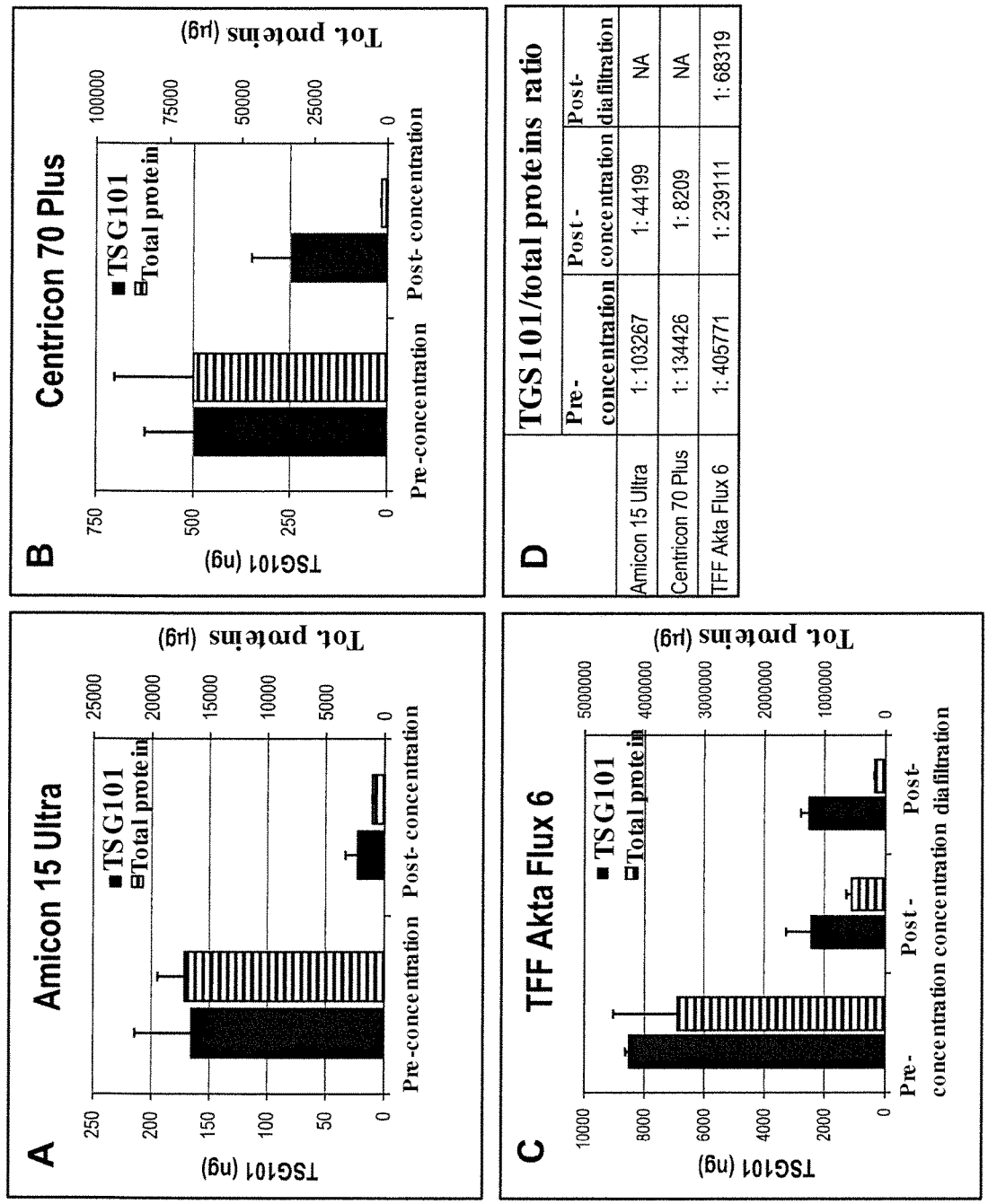
FIG. 11 shows the scale-up passage of concentrating the conditioned medium from exosomes.

Examples of results obtained with this method are reported in FIG. 11 (A, B, C) (total ng TSG101=ng/ml*ml sample).

Quantification of Total Proteins

The quantification of total proteins, in the initial conditioned medium and in the closed system purification products, may be performed with various commercial kits; in particular the QuantiPro™ BCA Assay Kit (Sigma-Aldrich Chemie GmbH) was used.

The samples to be quantified diluted in water or as such, are incubated with the kit reagents for the necessary time for the development of a colorimetric reaction. The reading of the absorbency at 562 nm of the sample is proportional to the quantity of proteins contained and, compared with a standard known quantity curve, allows the total desired content to be obtained, expressed in μg/ml.

Examples of results obtained with this method are reported in FIG. 11 (A, B, C) (total μg Total Proteins=μg/ml*ml sample).

Immunophenotypical Analysis of Exosomes

For the characterization of the molecules expressed on the surface of the exosomes, the MACSPlex Exosome Kit (Miltenyi Biotec) was used, which allows the analysis of 37 surface epitopes thanks to a combination of beads, characterized by different bond specificity and different fluorescence intensity, and a detection reagent. This kit was used following the manufacturer's instructions. In short, the exosomes are incubated with the beads to which they bond if they express specific epitopes. At the same time the detection reagent is also added, which bonds to the exosomes which in turn are "captured" by the beads. These complexes, formed by beads-exosomes-detection reagents, can be analyzed using a cytofluorimeter with a flow based on the fluorescence characteristics of the beads and the detection reagent. Positive signals in the different groups of beads indicate the presence of the corresponding surface epitope on the exosomes.

Exosome Functional Evaluation Test

Different tests in vitro can be used to have an indication of the cardioprotective activity of the exosomes. These tests envisage the use of cardiac muscle cells, which are treated so as to mime the cell damage due to myocardial infarction, and of substances able to detect the vitality and/or level of apoptosis of these cells. In our laboratory we have developed a functional test in which the vitality of human CPCs, treated with staurosporin (an antibiotic that induces apoptosis by inhibiting protein kinases) in a medium low in nutrients, is detected through the addition of calcein and propidium iodide. By adding the exosomes to these cultures, it is possible to have an estimate of their protective activity against apoptosis. At the end of the culture, cell vitality is estimated through a non-fluorescent derivative of calcein, which can be transported into the cell membrane of living cells where it is transformed into fluorescent calcein, and propidium iodide (PI), another fluorescent compound that can only pass through damaged cell membranes where it is inserted into the DNA.

The CPCs were plated 24 hours before the start of the test in 96-well plates in complete medium. At the start of the test the plate was washed and the cells were treated with staurosporin in a medium low in nutrients, with or without the addition of exosomes previously quantified with Nanosight. After 16 hours at 37° C., calcein and/or PI are administered to the cells and their fluorescence is detected through a plate reader (Infinite F200 Pro, Tecan Trading AG, Switzerland) after half an hour of incubation at 37° C.

Figure 12:
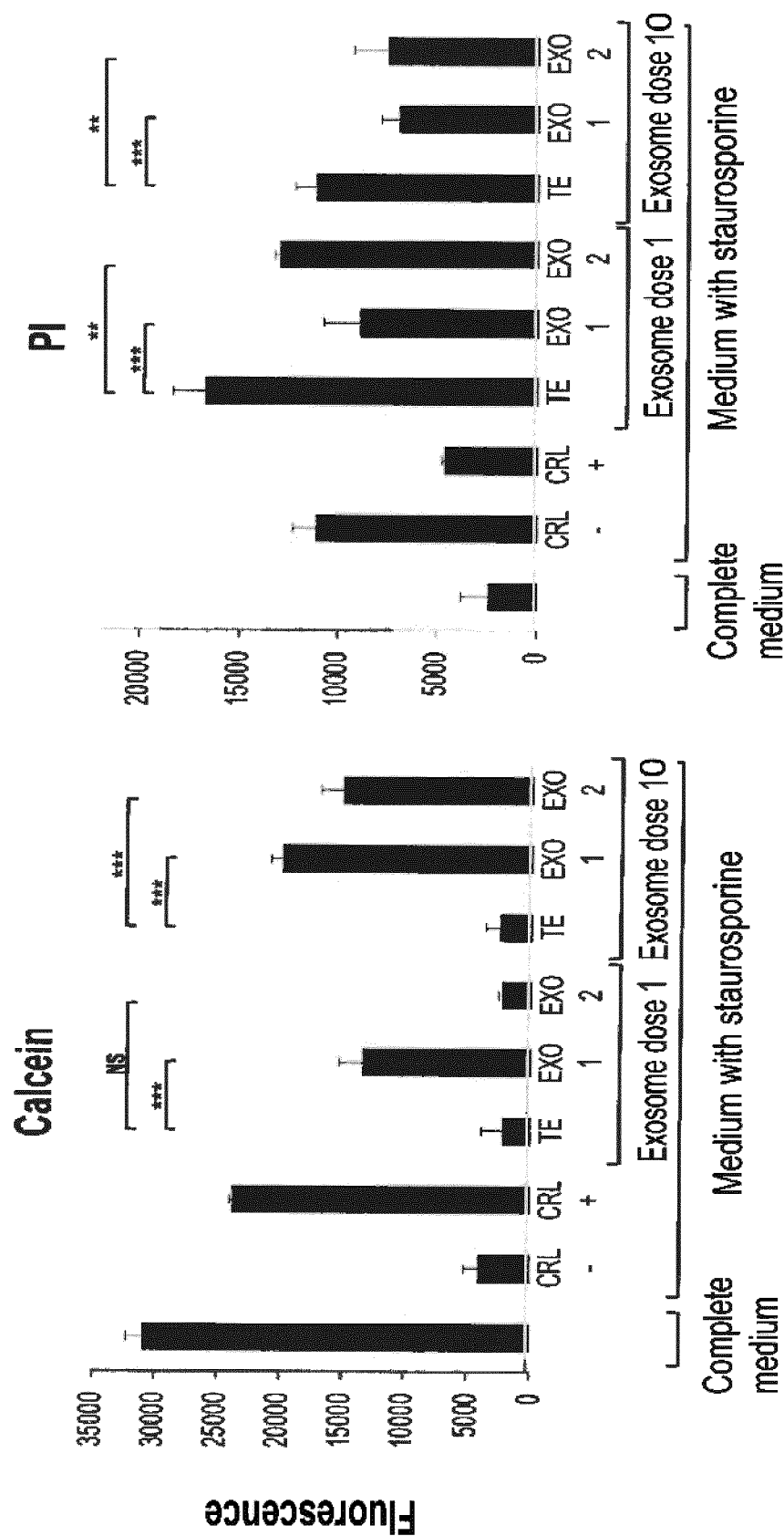
FIG. 12 shows the results obtained on the functionality of concentrated exosomes.

An example of results obtained with this test is reported in FIG. 12.

Final Considerations

Figure 2:
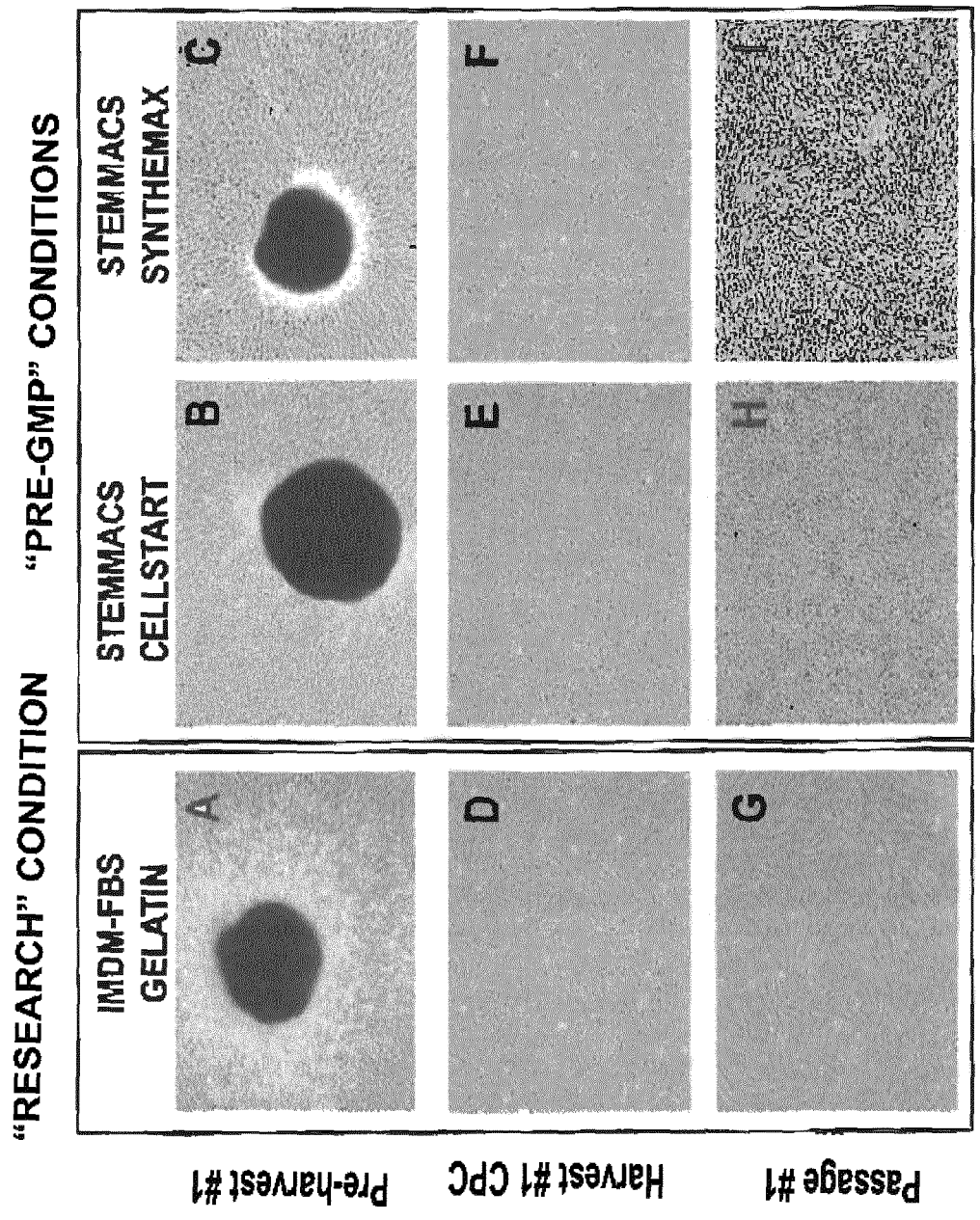
FIG. 2 shows optical microscope photographs of fragments of cardiac tissue from which the cardiac progenitor cells leak and of such cells in expansion.

The present invention shows in FIG. 2 images of cultures obtained from a representative cardiac tissue and shows that in pre-GMP conditions it is possible to isolate and expand CPCs in culture with similar morphological characteristics. With respect to "research grade" CPCs, the "pre-GMP" CPCs in passage 1 have smaller cell dimensions and grow more actively.

Figure 3:
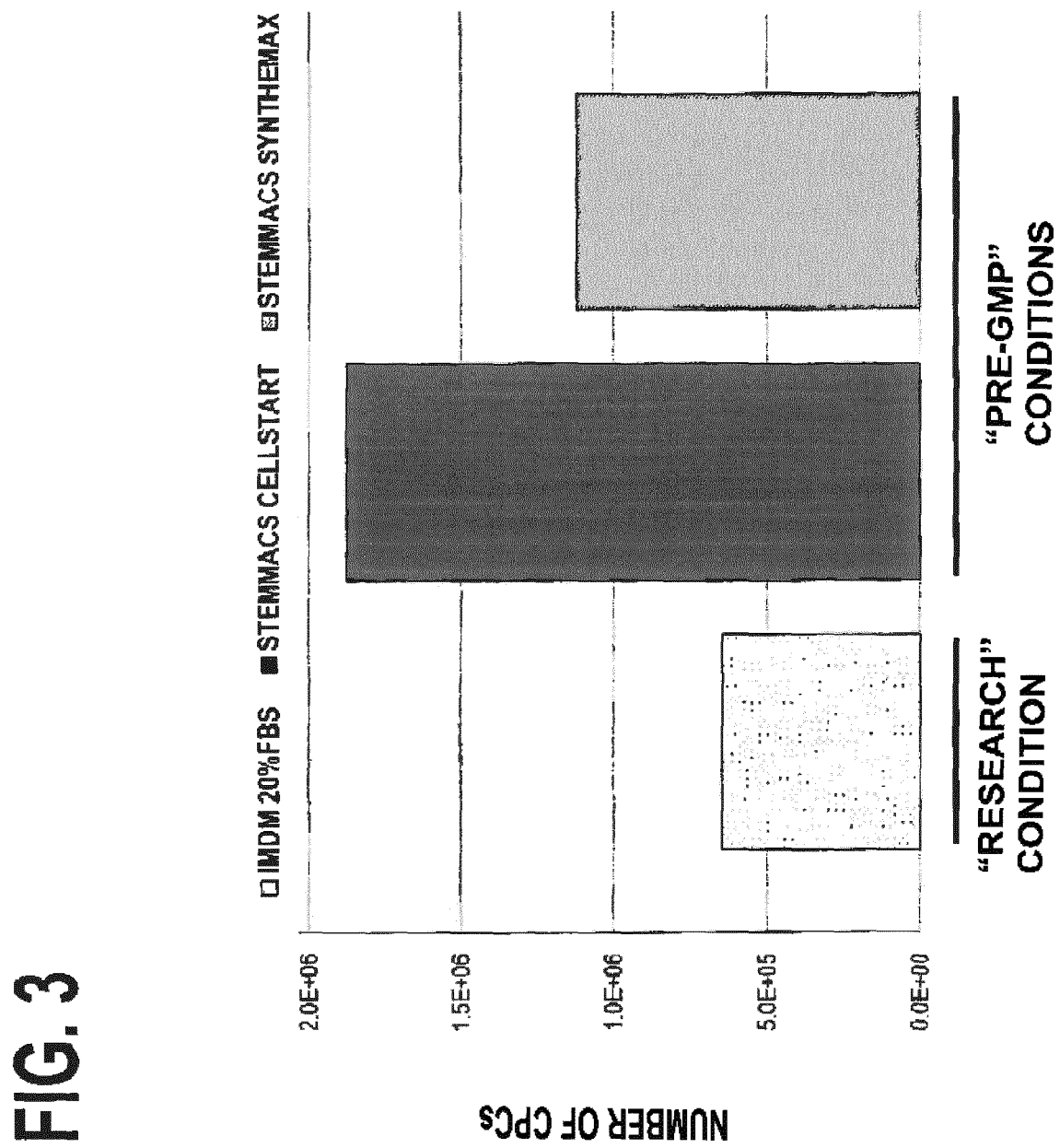
FIG. 3 shows a graph reporting the numbers of cardiac progenitor cells obtained both through the research grade process of the prior art and according to the present invention (PRE-GMP conditions).

Furthermore, as shown by the experiments reported in FIG. 3, the cell yield (average number of CPCs obtained at the first harvest, 5 experiments) is generally higher in "pre-GMP" conditions with respect to in the "research grade" condition.

Figure 4:
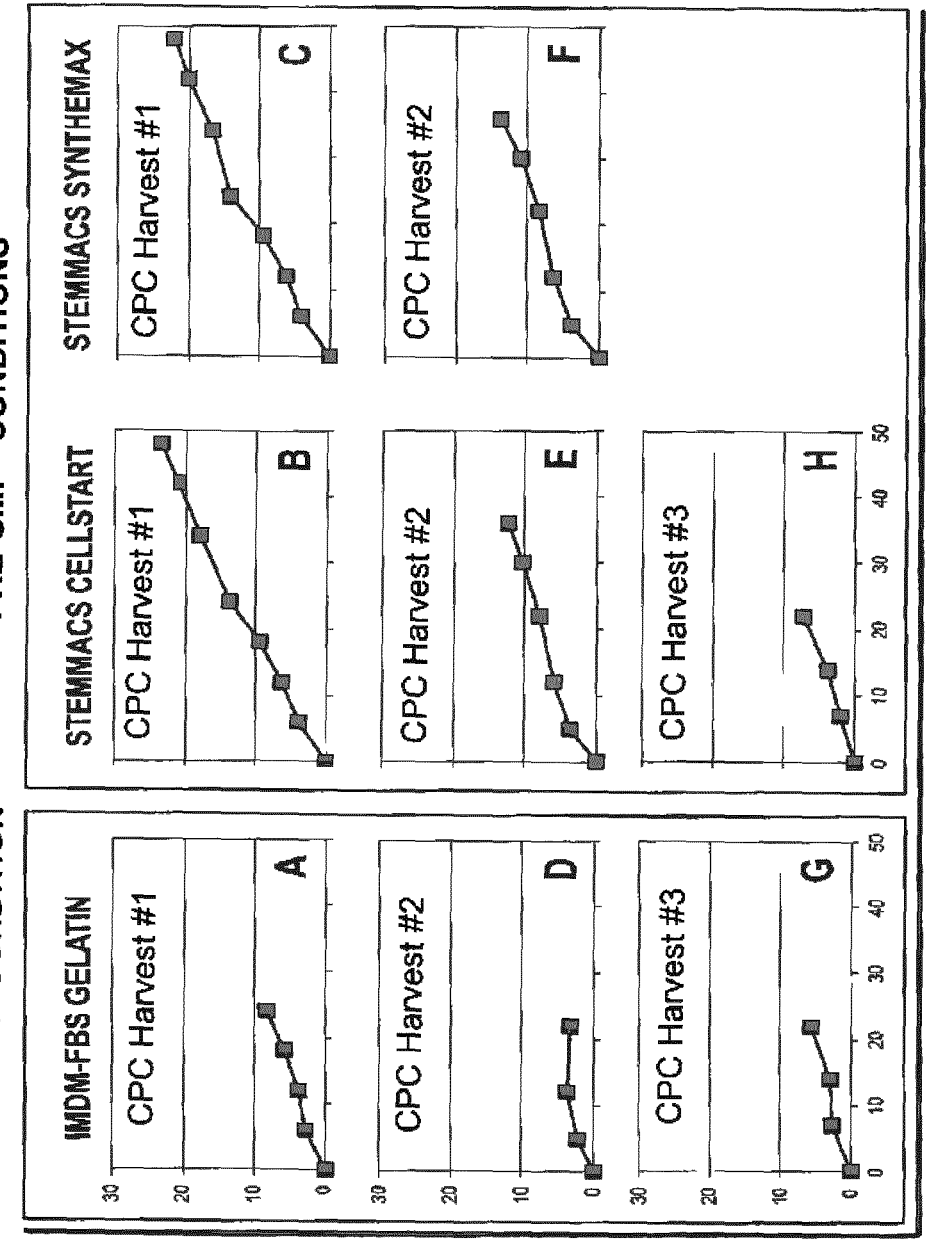
FIG. 4 shows the growth curves of cardiac progenitor cells both in "research grade" conditions and according to the present invention (PRE-GMP conditions).

Advantageously, as shown in FIG. 4, in "pre-GMP" conditions, the growth of CPCs is faster and the cells can be kept in culture longer with respect to in the "research grade" condition. In all conditions, the CPCs obtained at the first harvest show faster growth than those of the subsequent harvests.

Figure 5:
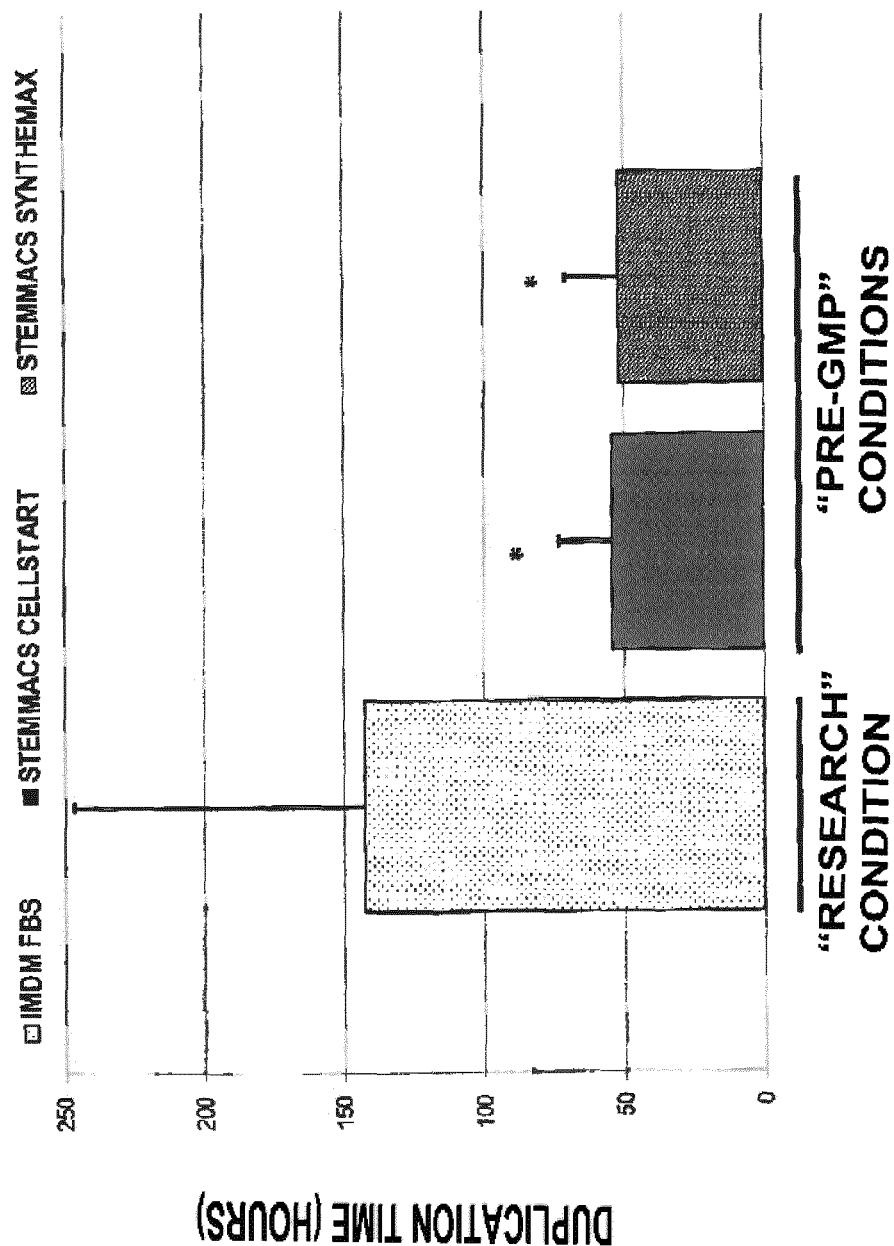
FIG. 5 shows a graph reporting the duplication times of cardiac progenitor cells both in "research grade" conditions and according to the present invention (PRE-GMP conditions).

FIG. 5 shows the duplication times of the CPCs obtained from the first harvest and it can be noted that the duplication times are significantly lower in "pre-GMP" conditions than in the "research" condition.

FIG. 6 shows that CPCs isolated and expanded in "pre-GMP" conditions (both STEMMACS CELL START and STEMMACS SYNTHEMAX), like those isolated and expanded in "research" condition (IMDM-FBS GELATIN) express typical markers of mesenchymal stem cells (CD105, CD73, CD90 variable), while they are negative for markers of hematopoietic lineage (CD14, CD20, CD34, CD45). The expression is maintained during the production of exosomes.

FIG. 7 shows that CPCs isolated and expanded in "pre-GMP" conditions (both STEMMACS CELL START and STEMMACS SYNTHEMAX), like those isolated and expanded in "research" conditions (IMDM-FBS GELATIN) express mesodermal (TBX-5, TBX-18) and cardiac-specific (GATA-4, MESP-1) transcription factors. The expression is maintained during the production of exosomes.

FIG. 8 shows the NTA (Nanoparticle Tracking Analysis) profiles of exosomes produced by CPCs of a representative donor, isolated and expanded in the different conditions. The profiles obtained in "pre-GMP" conditions (both STEMMACS CELL START and STEMMACS SYNTHEMAX) are more homogeneous than those obtained in "research" conditions (IMDM-FBS GELATIN), indicating an improvement in product quality.

Figure 9:
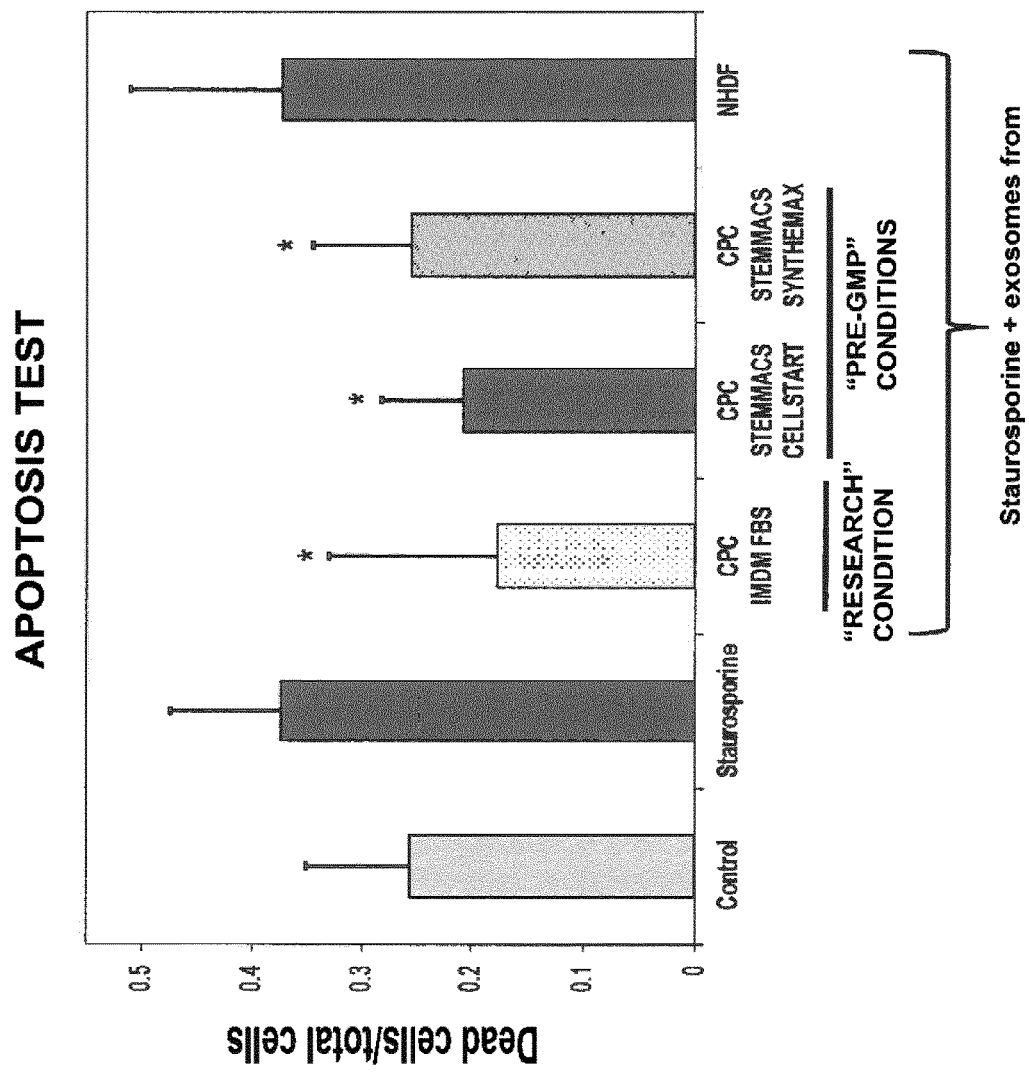
FIG. 9 shows the results obtained on the functionality of exosomes obtained from cardiac progenitor cells both in "research grade" and PRE-GMP conditions.

FIG. 9 indicates that exosomes from CPCs isolated and expanded both in "research" and "pre-GMP" conditions (both STEMMACS/CELLSTART and STEMMACS/SYNTHEMAX) significantly inhibit the apoptosis induced by staurosporine in cardiomyocytes.

The STEMMACS/CELLSTART condition was selected for the subsequent experiments being more efficient in supporting the adhesion of the tissue fragments in the initial stage of the process, an observation in line with the trend towards a higher cell yield (FIG. 3) with respect to the STEMMACS/SYNTHEMAX condition.

Therefore, the aim was to evaluate whether the CELLSTART substrate is necessary throughout the whole cell expansion step or only in the initial step of isolating CPCs.

Figure 10:
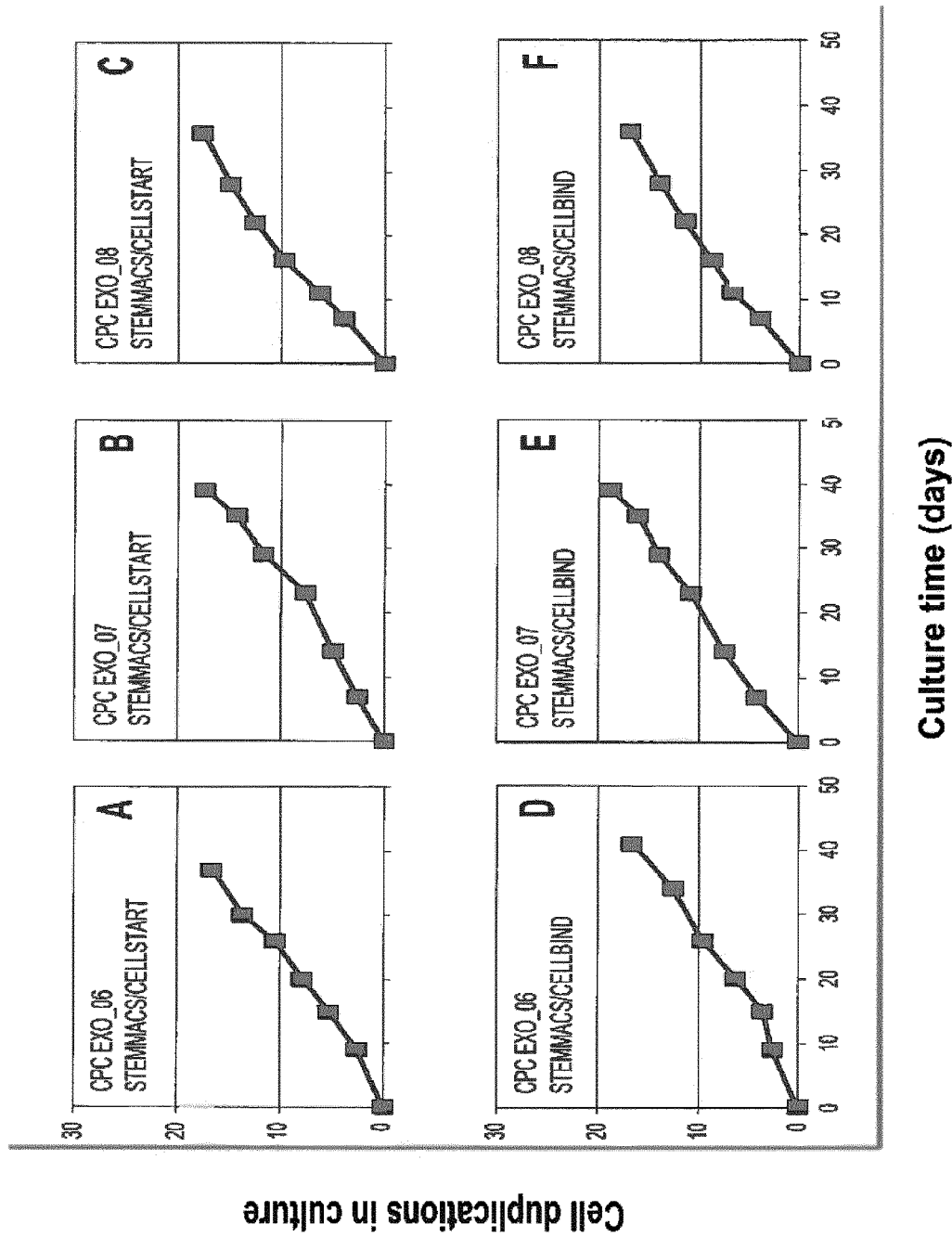
FIG. 10 shows the growth curves of the cardiac progenitor cells on different adhesion substrates.

FIG. 10 shows that CPCs isolated m STEMMACS/CELL-START can be expanded both by continuing the use CELL-START (panels A, B, C, cells obtained from 3 representative donors), and by transferring them into CELLBIND flasks (panels D, E, F, cells obtained from the same 3 donors).

The conditioned medium containing the exosomes was clarified through centrifugation and/or filtration (0.22 µm) to remove cell fragments, then concentrated through direct filtration with Amicon Ultra-15 or Centricon Plus 70 100 KD (Merck Millipore) or through tangential filtration with a UFP-300-C-2U hollow fiber module and AktaFlux (GE Healthcare) system, gradually performing a process scale up, from 10-15 mL (corresponding to about 150-200 ng total of TSG101) to 0.5 L of CM (corresponding to about 2500 ng total of TSG101). As process controls, tests were used for the quantification of the exosomal protein TSG-101 (ELISA) and the total proteins (see analytical methods chapter).

FIG. 11 shows the results in terms of TSG101 and total proteins pre- and post-concentration. A higher yield for TSG101 and for total proteins is observed in all cases indicating that the process is able to concentrate the exosomes and remove protein contaminants that are smaller than the cut-off used, with a consequent increase in purity, as indicated in the TSG10I/Total Protein ratio (FIG. 11 D). FIG. 12 shows that the concentrated exosomes are able to protect against CPC apoptosis in culture and against apoptosis induced by staurosporine (for the details of the test see the analytical methods chapter).

General Considerations on the Production and Quality Control Methods Described Above Advantages: integrated process that covers all the steps, from the handling of the starting tissue to the final medicinal product; use of high quality reagents and culture systems (absence of reagents or materials of animal origin), control strategy that aims to guarantee maximum quality for all the passages and for the medicinal product; large-scale CPC culture (from single biopsy ≥500E6 cells); high quality production system of conditioned medium containing exosomes (up to 8 L per batch; higher volumes with the use of a bioreactor); closed purification system for exosomes that comprises at least the following passages: clarification of the conditioned medium, concentration (TFF) on hollow fiber cartridge/membrane cassettes (at defined cut-off), diafiltration, any final filtration. In the purification process described here there may be further integrated passages, for example, based on the use of chromatography columns. The generation of a cell bank (MCB) allows the subsequent production of many batches of exosomes equivalent to each other and therefore the possibility to treat groups of patients in high numbers (e.g. advanced clinical phases or subsequent market) in an allogenic context.

This type of process could be applied not only to exosomes derived from CPCs but also to exosomes produced by other types of cells in culture (e.g. mesenchymal stem cells, muscle cells, fibroblasts, nervous system cells, dendritic cells, etc.) for different therapeutic uses.

The device and method for producing and purifying exosomes as they are conceived are susceptible to numerous modifications and variants, all falling within the inventive concept described and claimed.

The invention claimed is:

1. A device for producing and purifying exosomes from progenitor cells, wherein the device comprises a closed, sterile circuit having a pumping circuit and a plurality of serially connected processing stations, wherein
   a first processing station comprises a first culture medium containing said progenitor cells, which are cultured for the production of said exosomes;
   a second processing station comprises a second medium conditioned by the exosomes produced in the first processing station;
   a third processing station comprises a filter clarifying said conditioned medium;
   a fourth processing station comprises one or more hollow fiber cartridges concentrating the clarified conditioned medium by tangential filtration and a recirculator recirculating the concentrated medium for a subsequent concentration thereof;
   a fifth processing station comprises a formulation buffer diluting the concentrated medium;
   a sixth processing station comprises waste material output from said fourth processing station;
   a seventh processing station comprises a collector collecting the diafiltered-concentrated medium containing the purified exosomes; and
   an eighth processing station comprises a storage storing said purified exosomes.

2. The device for producing and purifying exosomes from progenitor cells according to claim 1, wherein said pumping circuit comprises at least one peristaltic or diaphragm pump.

3. The device for producing and purifying exosomes from progenitor cells according to claim 1, wherein said progenitor cells are cardiac progenitor cells.

4. The device for producing and purifying exosomes from progenitor cells according to claim 1, wherein said second processing station comprises a bag collecting said medium conditioned by said exosomes, said fourth processing station comprises a bag collecting said clarified conditioned medium, said fifth processing station comprises a bag that is sterilely connected to said formulation buffer, said sixth processing station comprises a bag collecting the waste material and said seventh processing station comprises a bag collecting said purified exosomes.

5. The device for producing and purifying exosomes from progenitor cells according to claim 1, wherein said recirculator comprises at least one peristaltic or membrane pump.

6. The device for producing and purifying exosomes from progenitor cells according to claim 1, wherein said hollow fiber has a cut-off comprised between 100 and 500 KD.

7. The device for producing and purifying exosomes from progenitor cells according to claim 6, wherein said hollow fiber has a cut-off of 300 KD.

8. The device for producing and purifying exosomes from progenitor cells according to claim 1, wherein said storage comprises vials made of polymer resistant to cryogenic temperatures.

* * * * *